(12) United States Patent
But et al.

(10) Patent No.: US 7,867,998 B2
(45) Date of Patent: Jan. 11, 2011

(54) METHOD OF MAKING ANTITUSSIVE MEDICINE AND RELIEVING COUGH

(75) Inventors: Pui-Hay Paul But, Hong Kong (CN); Yan-Tong Xu, Hong Kong (CN); Pang Chui Shaw, Hong Kong (CN); Ren Wang Jiang, Hong Kong (CN); Po Ming Hon, Hong Kong (CN)

(73) Assignee: Hong Kong Jockey Club Institute of Chinese Medicine Limited, Hong Kong (CN)

( * ) Notice: Subject to any disclaimer, the term of this patent is extended or adjusted under 35 U.S.C. 154(b) by 1078 days.

(21) Appl. No.: 11/224,165

(22) Filed: Sep. 12, 2005

(65) Prior Publication Data

US 2007/0060564 A1    Mar. 15, 2007

(51) Int. Cl.
*A61K 31/55* (2006.01)
(52) U.S. Cl. .................. 514/214.01; 424/725; 424/735
(58) Field of Classification Search .................. 514/212, 514/214.01; 424/735
See application file for complete search history.

(56) References Cited

U.S. PATENT DOCUMENTS

| 6,350,476 B1 * | 2/2002 | Hou ........................... 424/735 |
| 6,992,078 B2 | 1/2006 | Lin et al. |
| 2003/0229071 A1 * | 12/2003 | Lin et al. ................ 514/214.01 |

OTHER PUBLICATIONS

Helmer, "Treating Pediatric Cough with Qing Su Duan Ke Fang (Depurate & Stop Coughing Formula)," translating from Ming et al., "A Survey of the Therapeutic Efficacy of Treating 80 Cases of Pediatric Cough with Qing Su Duan Ke Fang (Dupurate & Stop Coughing Formula)," Hubei Journal of Chinese Medicine 2000: issue 5 at p. 396.*
Pilli et al., "Recent progress in the chemistry of the Stemona alkaloids." Nat. Prod. Rep. 2000:17; 117-127.*
Belvisi, et al., *Animal models of cough,* in Chung, et al., (Ed.), "Cough: Causes, Mechanisms and Therapy", Blackwell Publishing, Oxford, (2003) 217-222.
Brem, et al., "Feeding Deterrence and Contact Toxicity of Stemona Alkaloids—A Source of Potent Natural Insecticides", *J. Agricultural and Food Chemistry,* (2002) 50:6383-6388.
Chung, Hoi Sing, Ph.D. Thesis, "Chemical and Pharmacological Investigations into an Antitussive Traditional Chinese Medicinal Herb", The Chinese University of Hong Kong, (2001) (Abstract only).
Chung, et al., "Antitussive Activity of Stemona Alkaloids from *Stemona tuberosa*", *Planta Med,* (2003) 69:914-920.
English statement of relevance for Jiangsu New Medical College (Ed.) *Encyclopedia of Chinese Materia Medica,* Shanghai People's Press, Shanghai, (1977) 1:858-861.
Pilli, et al., "Recent progress in the chemistry of the *Stemona* alkaloids", *Nat. Prod. Rep.,* (2000) 17:117-127.
Xiang, et al., "Effects of airway inflammation on cough response in the guinea pig", *J. Appl. Physiol.,* (1998) 85:1847-1854.
Shinozaki, et al., "Inhibitory Actions of Tuberostemonine on the Excitatory Transmission at the Crayfish Neuromuscular Junction", Brain Research, 334, pp. 33-40, 1985.
Noro, et al., "A new alkaloid, croomine, from *Croomia heterosepala* Okuyama", Chem. Pharm. Bull., 27, pp. 1495-1497, 1979.
Cheng, et al., "A study of Stemona alkaloids, III. Application of 2D-NMR spectroscopy in the structure determination of stemoninine", J. Nat. Prod., 51, pp. 202-211, 1988.
Karlsson, et al., "Pharmacological Regulation of the Cough Reflex—from Experimental Models to Antitussive Effects in Man", Pulmonary Pharamcology and Therapeutics, 12, pp. 215-238, 1999.

* cited by examiner

*Primary Examiner*—Frederick Krass
*Assistant Examiner*—Walter E Webb
(74) *Attorney, Agent, or Firm*—George G. Wang; Wilkinson & Grist

(57) ABSTRACT

Method for relieving cough using an effective antitussive chemical compound belonging to stemoamide or tuberostemospironine and method for manufacturing pharmaceutical compositions for treating or relieving cough in human and animal subjects which including a stemoamide or tuberostemospironine compound. In addition, the antitussive property of the compounds provides a method for assessing the quality of herbs traditionally used in treating cough by analyzing the content of the effective chemical ingredient, i.e., compounds of stemoamide type and/or tuterostemospironine type. It further provides a method for identifying medicinal herbs which may be used for relieving cough by phytochemical determination of the existence of compounds that are of stemoamide or tuterostemospironine type.

11 Claims, 5 Drawing Sheets

Antitussive effects of neotuberostemonine (*i.g.*)
* P<0.05, ** P<0.01 (n=6. paired-T test)
Note: blank column: 1$^{st}$ challenge, black column: 2$^{nd}$ challenge Antitussive effects of croomine (*i.g.*)
* $P<0.05$, ** $P<0.01$ (n=6, paired-T test)
Note: blank column: $1^{st}$ challenge, black column: $2^{nd}$ challenge Antitussive effects of stemoninine (*i.g.*)
** $P<0.01$ (n=6, paired-T test)
Note: blank column: 1st challenge, black column: 2nd challenge Stenine group (I)

Stemoamide group (II)

Tuberostemospironine group (III)

Stemoamine group (IV)

Parvistemoline group (V)

HPLC chromatograms for the *Stemona japonica* (a), *S. sessilifolia* (b) and *S. tuberosa* (c) showing croomine (1) and stemoninine (2)

METHOD OF MAKING ANTITUSSIVE MEDICINE AND RELIEVING COUGH

FIELD OF THE INVENTION

This invention relates to a method for preparing effective antitussive drugs and for relieving cough in human or animal subjects. Particularly, it relates to antitussive pharmaceutical compositions containing one or more stemoamide type compounds and/or one or more tuberostemospironine type compounds and their use for relieving cough. The invention also relates to a method for quality control of herbs traditionally used in treating cough in the East by analyzing the content of effective chemical ingredient. It further relates to a method for identifying medicinal herbs for use in relieving cough by phytochemical determination of the existence of compounds that are of stemoamide or tuberostemospironine type.

BACKGROUND OF THE INVENTION

Cough is one of the most common complaints for which medical attention is sought. It can be divided into acute and chronic cough according to their duration. Acute cough, lasting less than 3 weeks, is most often due to an acute viral upper respiratory tract infection and is usually transient and self-limited. Chronic cough, always lasting 8 weeks or longer, is mainly due to one or more of three aetiologies: post-nasal drip syndrome (PNDS), asthma, and gastro-oesophageal reflux disease (GORD). It has been demonstrated that specific treatment of an established aetiology of cough is highly successful. However, nonspecific antitussive therapy aiming at suppressing the sensitivity of the cough reflex regardless of the underlying aetiology of cough, is often ineffective.

Currently available nonspecific therapy is limited by lack of effective medications and/or their unacceptable or intolerable side effects. Epidemiological data from the over-the-counter (OTC) market showed that hundreds of millions of pounds in the UK and several billion dollars in the United States were spent on cough/cold. Although over 50 antitussive drugs are used in current clinical practices, a recent study suggests that OTC antitussive drugs possess little clinically relevant efficacy. Currently the most effective nonspecific antitussive agents are opiates. Almost all opiates have antitussive activity, but only those with weak analgesic activity are generally used as antitussives. An example of this type of medicine is codeine which is suitable for the treatment of dry cough that is interfering with rest or sleep. At high doses, codeine may cause sleepiness, addiction, constipation, respiratory depression and hypotension. It should not be used during pregnancy. Thus, there is current need for more effective nonspecific antitussive agents.

A number of herbs have a rich history of use for treating coughs due to colds, bronchitis, or other mild conditions. Among those herbs that have been shown to have some cough-relieving activity are marshmallow, sundew, and coltsfoot. They have been used in many parts of the world.

Phytochemical study of traditional herbal medicine has demonstrated other types of chemical compounds also have beneficial antitussive activity with less side-effect than the above-mentioned synthetic compounds. For example, neotuberostemonine isolated from Radix Stemonae, which is the root tuber of *Stemona* species recognized in the Pharmacopoeia of the People's Republic of China, was demonstrated to have strong antitussive effects. Furthermore, it is believed that neotuberostemonine does not act on opiate receptors while it has an antitussive potency comparable to that of codeine. Neotuberostemonine is believed to have no side-effect associated with the action on opiate receptors.

Many phytochemical studies on *Stemona* species have been reported. 52 alkaloids have been isolated and identified from Radix Stemonae and they are divided into five groups and a miscellaneous group according to molecular structures. The five groups are stenine, stemoamide, tuberostemospironine, stemoamine and parvistemoline (FIG. 4). Phytochemical analysis on five species of *Stemona* collected from different provinces and over 30 samples of Radix Stemonae from different herbal markets in China revealed that neotuberostemonine was present in only two samples. The results suggested that neotuberostemonine is present only in isolated samples of *Stemona tuberosa*, not universally present in *Stemona*. Therefore, neotuberostemonine cannot serve as a biomarker to indicate whether an herb can be useful as an antitussive agent. Another problem is that there may not be abundant raw material available for preparing neotuberostemonine as antitussive medicine.

It is an object of the present invention to obtain another group or groups of chemical compounds more universally existing in *Stemona* that provide main basis for the antitussive effects observed for most *Stemona* species. The new type(s) of compounds is to be used to make antitussive products to relieve cough and to serve as biomarkers in assessing the quality of the herbs used for relieving cough and in searching other herbs whose antitussive activity is so far unknown.

SUMMARY OF THE INVENTION

The present invention provides a method of making antitussive product compositions for relieving cough of human or animals using one or more chemical compounds belonging to two chemical groups, the stemoamide group and the tuberostemospironine group, and a method of establishing and using the two groups of compounds as a biomarker to indicate the quality of the herbs traditionally used for treating or relieving cough and/or to help identify new antitussive herbs which are not traditionally known or used for treating or relieving cough.

The first group of the compounds utilized in the present invention having the following base structure I:

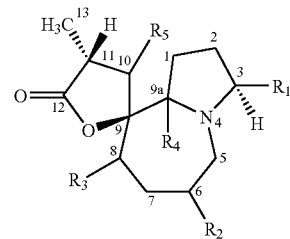

The second group of the compounds utilized in the present invention having the following base structure II:

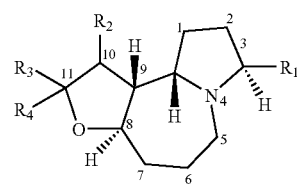

For both groups, it is contemplated, as it would be contemplated by people with ordinary skill in the field of organic chemistry or medicinal chemistry, that various substitutes may be attached to the base structure by substitution at various positions. Such substitutions are routinely performed by people engaged in medicinal chemistry in searching for compounds better than the base compounds themselves in terms of better therapeutic effects, less side-effects, less expensive to synthesize or other advantages. The present invention also contemplates that for the purpose of practicing the present invention the stemoamide and tuberostemospironine compounds may be partially or substantially purified and isolated from natural resources, such as from herbs, or may be obtained through chemical synthesis.

Exemplary compounds with base structure I include, but are not limited to:

Croomine: $R_1$=α-methyl-γ-butyrolactone, $R_2$=H, $R_3$=H, $R_4$=H, $R_5$=H

6-Hydroxycroomine: $R_1$=α-methyl-γ-butyrolactone, $R_2$=OH, $R_3$=H, $R_4$=H, $R_5$=H Stemospironine: $R_1$=α-methyl-γ-butyrolactone, $R_2$=H, $R_3$=OCH$_3$, $R_4$=H, $R_5$=H 10-Hyroxycroomine: $R_1$=α-methyl-γ-butyrolactone, $R_2$=H, $R_3$=H, $R_4$=H, $R_5$=OH Tuberostemospironine: $R_1$=carbonyl, $R_2$=H, $R_3$=H, $R_4$=H, $R_5$=OH Other suitable substitutions on base structure I are contemplated as follows:

$R_1$ is selected from the group consisting of H (hydrogen), =O (carbonyl), OH (hydroxyl), OCH$_3$ (methoxy) and

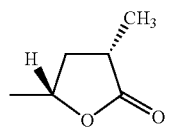

(α-methyl-γ-butyrolactone);

$R_2$ is selected from the group consisting of H (hydrogen), OH (hydroxyl), OCH$_3$ (methoxy) and —O—(oxygen bridge to $R_4$);

$R_3$ is selected from the group consisting of H (hydrogen), OH (hydroxyl) and OCH$_3$ (methoxy);

$R_4$ is H (hydrogen) or —O—(oxygen bridge to $R_2$)

$R_5$ is H (hydrogen), OH (hydroxyl) or OCH$_3$ (methoxy)

Exemplary compounds for group II include, but are not limited to:

Stemoninine:

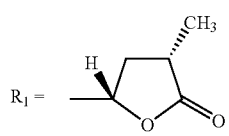

$R_2$=CH$_2$CH$_3$, $R_3$,

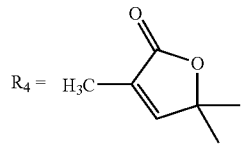

Tuberostemoamide $R_1$=O, $R_2$=CH$_2$CH$_3$,

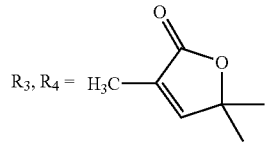

$R_3$, $R_4$ =

Other suitable substitutions on base structure II are contemplated as follows:

$R_1$ is selected from the group consisting of H (hydrogen), =O (carbonyl), OH (hydroxyl), OCH$_3$ (methoxy) and

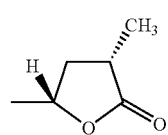

(α-methyl-γ-butyrolactone).

$R_2$ is selected from the group consisting of H (hydrogen), CH$_3$ (methyl), CH$_2$CH$_3$ (ethyl) and CN (cyano).

$R_3$ and $R_4$ are each independently selected from the group consisting of H (hydrogen), =O (carbonyl), and —O—C(=O)—C(CH$_3$)=C—, which form an monosubstituted spirolactone ring fused at C-11 to form

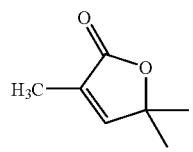

(3-methyl-5H-furan-2-one), or —O—C(=O)—C(CH$_3$)=C(OCH$_3$)—, which form an disubstituted lactone ring attached to C-11 by a double bond to form

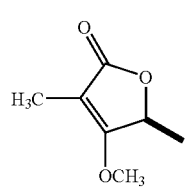

(4-methoxy-3-methyl-5H-furan-2-one)

It is further contemplated, as a person with ordinary skill in the art would understand, that the above compounds may be made in various possible racemic, enantiomeric or diastereoisomeric isomer forms, may form salts with mineral and organic acids, and may also form derivatives such as N-oxides, prodrugs, bioisosteres. "Prodrug" means an inactive form of the compound due to the attachment of one or more specialized protective groups used in a transient manner to alter or to eliminate undesirable properties in the parent molecule, which is metabolized or converted into the active compound inside the body (in vivo) once administered. "Bioisostere" means a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Making suitable prodrugs, bioisosteres, N-oxides, pharmaceutically acceptable salts or various isomers from a known compound (such as those disclosed in this specification) are within the ordinary skill of the art. Therefore, the present invention contemplates all suitable isomer forms, salts and derivatives of the above disclosed compounds.

Two particular compounds are provided as specific embodiments to demonstrate and enable the practice of the invention. Their structures are as follows:

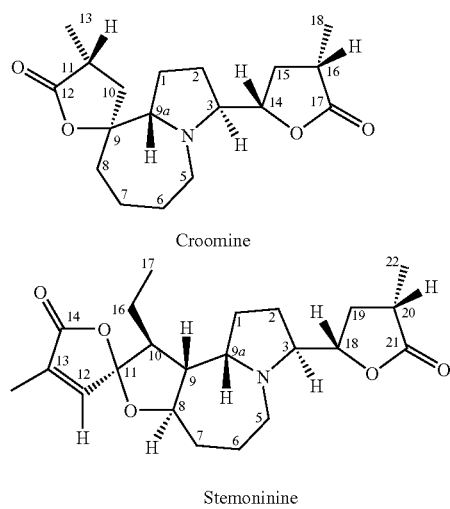

Croomine

Stemoninine

According to the present invention, various product compositions and formulations containing one or more of the stemoamide and/or tuberostemospironine compounds may be manufactured and used in treating or relieving cough, such as, for example, pills, capsules, injections, or any other suitable dosage forms. In addition, the antitussive compounds may also be administered in the form of liposome delivery systems. The process and technology for manufacturing those pharmaceutical compositions and formulations (dosage forms) are conventional or known in the art. As those processes are not part of the invention, they do not serve as limitations to the scope of the invention.

As another aspect of the present invention, a method is provided for assessing the quality of herbs traditionally known or used for relieving cough by measuring the content of the chemical compounds belonging to one of the two chemical groups with base structure I or II, respectively. As a preferred example, either croomine or stemoninine may be used for practicing the method.

As a further aspect of the present invention, a method is provided for searching or identifying antitussive herbs which are not known or have been used for treating cough by measuring the content of the chemical compounds belonging to one of the two chemical groups with base structure I or II, respectively. As a preferred example, either croomine or stemoninine may be used for practicing the method.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF THE PRESENT INVENTION

Isolation of Croomine and Stemoninine

Figure 1:
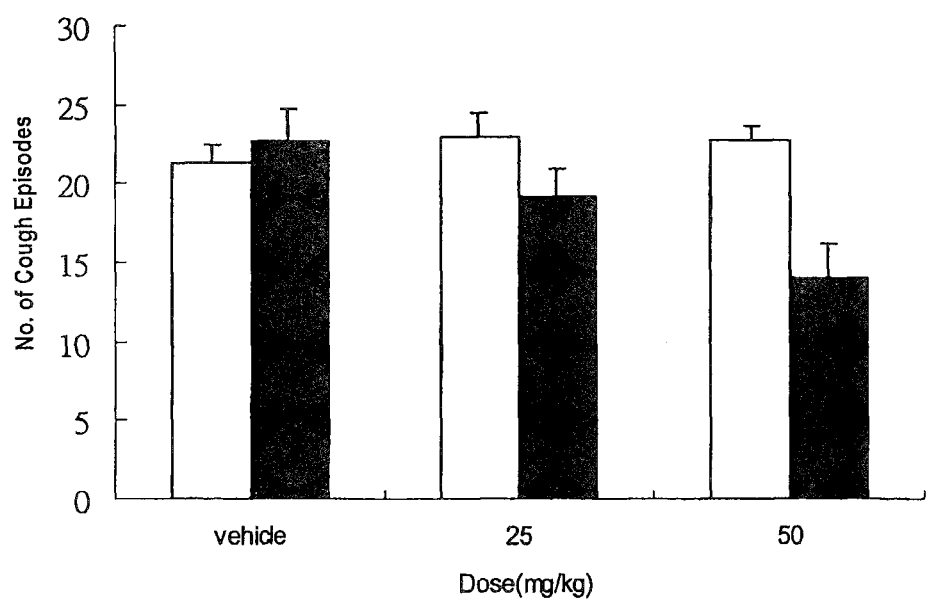
FIG. 1 shows the antitussive effect of neotuberostemonine (an effect known in the prior art).

Croomine and stemoninine can be extracted readily from Radix Stemonae, which is available on open market. One method is described below: dried root tubers of Radix Stemonae are chopped into small cubes and extracted twice with 95% EtOH under reflux for two (2) hours. The extracts are collected and pooled together, and then dried under reduced pressure. The syrup residue is dissolved with 4% HCl and then filtered. The acidic filtrate is extracted with $Et_2O$ and $CH_2Cl_2$ successively. The $CH_2Cl_2$ layer will give a crude alkaloid fraction 1. The acidic aqueous phase is basified to pH 9 with 35% $NH_4OH$ and then extracted with $Et_2O$. The $Et_2O$ is evaporated to afford a crude alkaloid fraction 2. The crude alkaloid fraction 1 and 2 are chromatographed through silica gel column with a mixture solvent of hexane and EtOAc (4:6) as an eluant and monitored by TLC. Fraction 1 yields a syrup alkaloid identified as stemoninine (2). Fraction 2 affords a light yellow oil identified as croomine (1).

Identification of Stemoninine and Croomine

Croomine (1): an oil. UV: no. EI-MS m/z: 321 [M]+. 290, 222 [M-C5H7O2]+(100), 194, 124, 110; $^1$H NMR (300 MHz, pyridine $-d_5$) and $^{13}$C NMR (75 MHz, pyridine $-d_5$) (δ): in Table 1. These spectra data were identical with the data reported for croomine [Noro, T., Fukushima, S., Ueno, A., Miyase, T., Iitaka, Y., Saiki, Y., A new alkaloid, croomine, from *Croomia heterosepala* Okuyama. *Chem. Pharm. Bull.* 1979, 27, 1495-1497].

Stemoninine (2): clear syrup. UV: no. EI-MS m/z: 389[M]+, 290 [M-C5H7O2]+(100), 276, 246, 178, 84, $^1$H NMR (500 MHz, pyridine $-d_5$) (δ) and $^{13}$C NMR (125 MHz, pyridine $-d_5$) (δ): in Table 1. These spectra data were identical with the data reported for Stemoninine [Cheng, D., Guo, J., Chu, T. T., Roeder, E. A study of *Stemona* alkaloids, III. Application of 2D-NMR spectroscopy in the structure determination of stemoninine. *J. Nat. Prod.* 1988, 51, 202-11].

TABLE 1

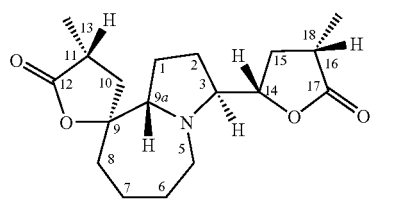

1

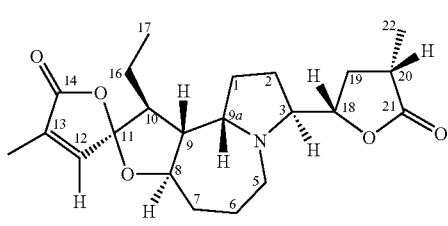

2

The 1H NMR and 13C NMR data of alkaloid 1 and 2†

| | Stemoninine (2) | | Croomine (1) | |
|---|---|---|---|---|
| | $^1$H | $^{13}$C | $^1$H | $^{13}$C |
| 1 | 1.35, 1H, m<br>1.73, 1H, m | 26.63, t | 1.34-1.65, 2H | 27.80 |
| 2 | 1.5, 1H, m<br>1.75, 1H, m | 26.76, t | 1.34-1.65, 2H | 26.83 |
| 3 | 3.20, 1H, m | 63.31, d | 3.25, 1H, m | 69.52 |
| 5 | 2.88, 1H, dd (5.5, 11.5)<br>3.45, 1H, dd(15.5, 6.9) | 45.46, t | 3.09, 2H, m | 48.82 |
| 6 | 1.57, 1H, m<br>1.63, 1H, m | 20.75, t | 1.34-1.65, 2H, m | 22.54 |
| 7 | 1.43, 1H, m<br>2.05, 1H, m | 36.03, t | 1.34-1.65, 2H | 28.22 |
| 8 | 3.99, 1H, ddd | 81.47, d | 1.34-1.65, 2H | 35.15 |
| 9 | 2.45, 1H, m | 53.42, d | | 89.53 |
| 9a | 3.68, 1H, m | 58.44, d | 3,39, 1H, t(7.2) | 67.31 |
| 10 | 2.05, 1H, m | 51.23, d | 2.33, 1H, dd(13.8,15.9)<br>1.7-1.9, 1H | 36.42 |
| 11 | | 114.32, s | 2.77, 1H, m | 41.4 |
| 12 | 6.92, 1H, d(2.0) | 145.93, d | | 179.6 |
| 13 | | 133.44, s | 1.24, 3H, d, (7.5) | 18.01 |
| 14 | | 171.90, s | 4.22, 1H, ddd, (6.6,5.0,10.0) | 81.15 |
| 15 | 1.84, 3H, s | 10.43, q | 2.14, 1H, m<br>1.7-1.9, 1H, | 35.38 |
| 16 | 1.35, 1H, m<br>1.57, 1H, m | 20.61, t | 2.62, 1H, m | 37.8 |
| 17 | 0.77, 3H, t(7.2) | 12.99, q | | 179.8 |
| 18 | 4.17, 1H, m | 83.24, d | 1.18, 3H, d(6.9) | 15.30 |
| 19 | 1.43, 1H, m<br>2.31, 1H, m | 34.23, t | | |
| 20 | 2.58, 1H, m | 35.06, d | | |
| 21 | | 179.52, s | | |
| 22 | 1.21, 3H, d(7.0) | 15.08, g | | |

HPLC Analysis

For sample preparation, a small amount of chopped roots (5 g) of *Stemona tuberosa* was refluxed with 95% ethanol (100 ml) for an hour. The extracted solution was condensed under reduced pressure to afford a residue which was dissolved in 4% HCl (50 ml) and filtered. The filtrate was basified with 25% ammonium solution to pH 9 and extracted with $CH_2Cl_2$. The extract was condensed and dissolved in methanol (2 ml) to afford the total alkaloid solution. For the methanol crude extract, the chopped roots (2 g) was extracted with methanol (5 ml) under ultrasonic condition for an hour. Both the final solutions were filtered through a 0.22 μm PTFE syringe filter, and an aliquot of each filtrate (10 μl) was injected in the HPLC instrument for analysis. This process may be used, with or without modification, for qualitatively or quantitatively analyzing the antitussive compounds newly identified in the present invention. Such analysis provides a method for assessing the quality of the herbs traditionally used for relieving cough. It also provides method for searching other herbs whose antitussive activity is so far unknown.

Analytical HPLC was performed on a Beckman System Gold instrument equipped with a 125 solvent module, a 168 photo diode array detector and a 508 autosampler, and coupled with an Alltech 500 ELSD detector (evaporative light scattering detection) (Alltech, Deerfield, Ill., USA) and a nitrox nitrogen generator. Chromatographic separation was carried out on a C18 column (150×4.6 mm, 3 μm; Alltech, USA), using a isocratic solvent system comprised of acetonitrile-water (40:60, v/v) containing 0.12% $Et_3N$ with a flow rate of 1.0 ml/min. Temperature for the ELSD drift tube was set at 97° C. and the nitrogen flow was 2.6 SLPM (standard liters per minute). Of course, people of ordinary skill in the art may find other equipment and/or conditions would also produce satisfactory results.

Antitussive Assay

Unrestrained conscious guinea pigs were individually placed in a transparent Perspex airtight chamber and exposed to 0.5 M citric acid aerosol produced by an ultrasonic nebulizer (NEU12, Omron, Tokyo, Japan) for 10 min with a flow rate of 0.6 ml/min. During the 10 min observation period, the animals were continuously observed, and the numbers and timing of typical body movement of cough responses including opening the mouth, contraction of thoracic and abdomen muscles and a jerking of the front body were noted. The cough sounds were concurrently picked up via a microphone which connected to a personal computer and analyzed by Cool Edit 2000 software (Syntrillium, Phenix, USA). Thus a cough response can be differentiated from a sneeze and other background noises by observation of body movements, cough sound from loudspeakers and wave patterns recorded in the computer. Animals producing cough more than 18 times but less than 30 in the first challenge were selected for further antitussive tests. Cough episodes during the first challenge were recorded as control data. After 72 hour recovery, the selected sensitive animals were randomly divided into several groups with six animals in each group. The test samples were changed to their salt forms with 4% HCl to dissolve in saline and administrated intragastrically.

Antitussive Properties of Croomine and Stemoninine

Figure 2:
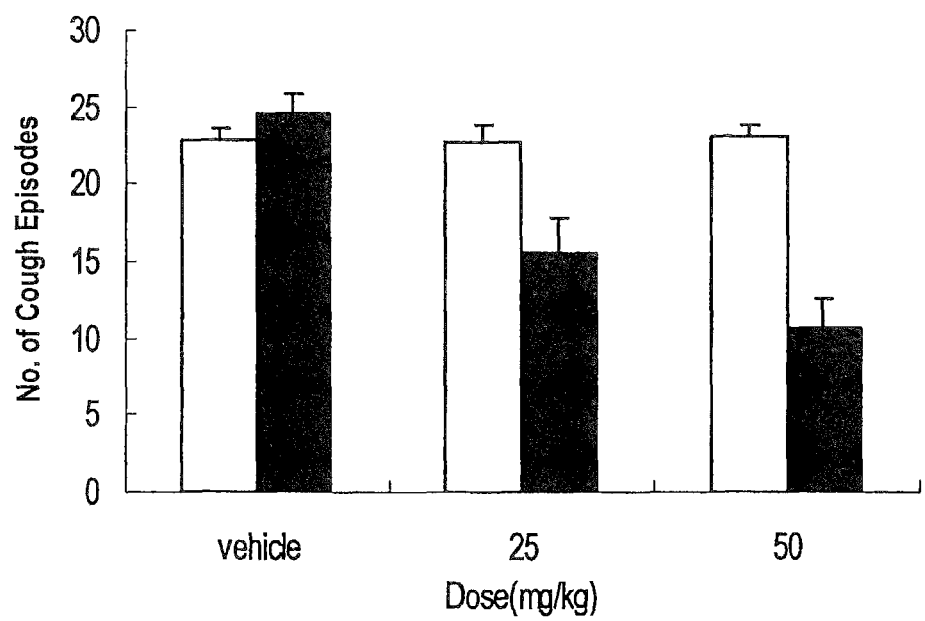
FIG. 2 shows the antitussive effect of croomine.
Figure 3:
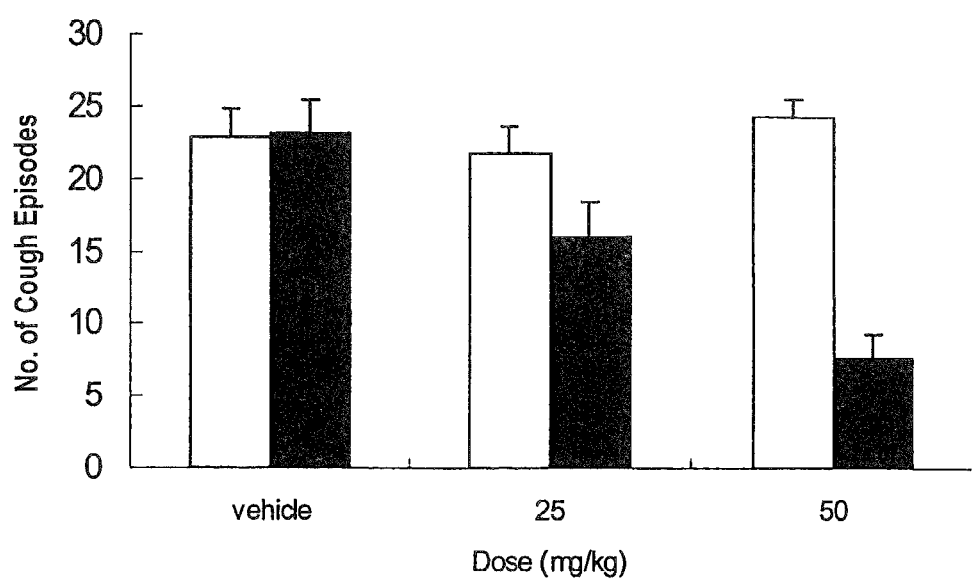
FIG. 3 shows the antitussive effect of stemoninine.
Figure 4:
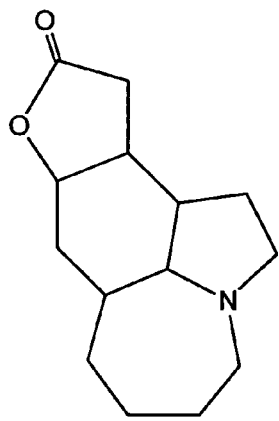
FIG. 4 lists five groups of alkaloids which have been isolated and identified from Radix Stemonae (prior art).
Figure 4:
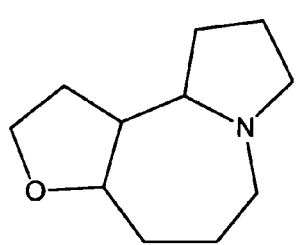
Figure 4:
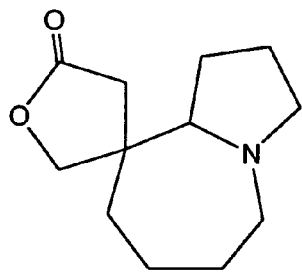
Figure 4:
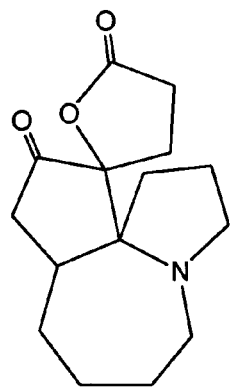
Figure 4:
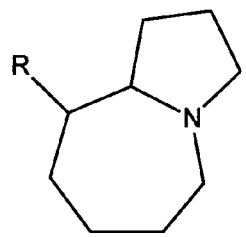
Figure 5A:
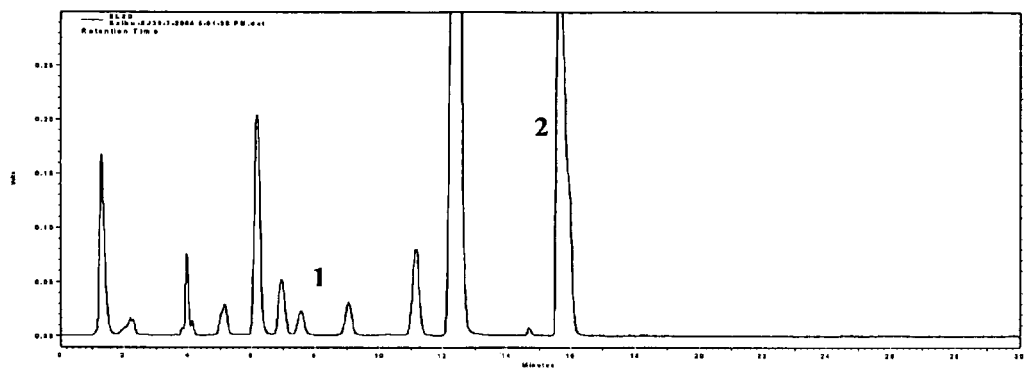
FIGS. 5a-c are HPLC chromatograms showing the presence of croomine and stemoninine in three *Stemona* species. *S. japonica*, *S. sessilifolia* and *S. tuberosa*.
Figure 5B:
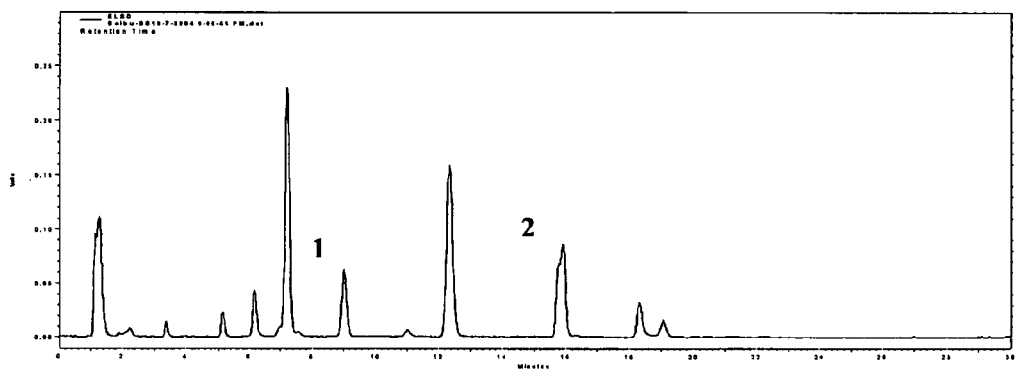
Figure 5C:
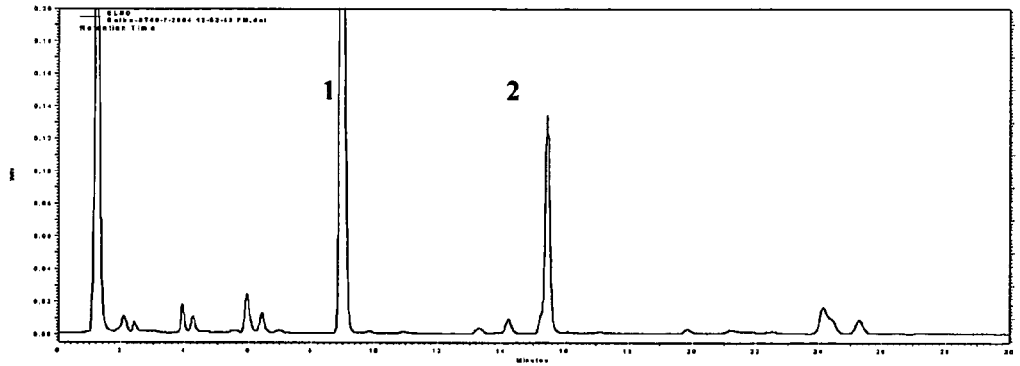

In the present experiments, neotuberostemonine produced a reduction in cough episodes by 17 and 40% (P<0.01 versus 1st challenge) at 25 and 50 mg/kg i.g., respectively. This reduction was lower than the 85% inhibition previously demonstrated by intraperitoneal experiments at the same dosage (Chung, et al., 2003 [Chung, H. S., Hon, P. M., Lin, G., But, P. P. H., Dong, H., Antitussive activity of *Stemona* alkaloids from *Stemona tuberosa*. Planta Med., 2003, 69, 914-920.]. This is possibly due to the lower bioavailability through intragastric administration than through intraperitoneal administration. On the other hand, at 25 and 50 mg/kg i.g., as shown in FIG. 2, croomine reduced the cough episodes by 35 and 57%, respectively. Stemoninine showed similar high potency at the same dose levels, lowering the cough episodes by 32 and 66%, respectively, as shown in FIG. 3. These results suggested that the two alkaloids had similar antitussive potency, which is stronger than that of neotuberostemoine. These two alkaloids are different from neotuberostemonine in molecular skeletons (i.e., base structures). Neotuberostemonine belongs to the stenine group while croomine and stemoninine belong to the tuberostemospironine and stemoamide groups, respectively. These results indicated that the two groups of alkaloids other than stenine type also have antitussive properties, and thus enriched the antitussive spectrum of Stemona alkaloids. It is the first time to demonstrate their antitussive effects with potency comparable to stenine alkaloids. Since croomine and stemoninine are the major components of Radix Stemonae, they provided scientific evidence for the use of Radix Stemonae for cough treatment in folk medicines and in PRC Pharmacopeia.

Manufacturing Pharmaceutical Compositions and their Uses in Relieving Cough

Once the effective chemical compound is identified and partially or substantially pure preparations of the compound are obtained either by isolating the compound from natural resources such as herbs or by chemical synthesis, various pharmaceutical compositions or formulations can be fabricated from substantially pure compound or partially pure preparation of the compound (such as herbal extract) using the presently established process or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more conventional processes established in the industry to the practice of the present invention. Alternatively, people of ordinary skill in the art may modify the existing conventional processes to better suit the antitussive compounds identified by the present invention. For the purpose of defining the scope of the present invention, the term "herbal extract" means a mixture of natural occurring compounds obtained from herb materials via an extracting process, in which at least 80% (w/w) of the mass are unidentified compounds. The extracting process involves immersing raw herb material(s) in a solvent (commonly, alcohol and/or water) for a predetermined length of time, separating the solvent from the raw herb material(s) and then removing the solvent to obtain an herb extract. Additional partial purification steps may be included in an extract process. The antitussive pharmaceutical composition of the present invention is not a direct product of the extracting process. It is not an herbal extract itself, although one or more herbal extracts may be added as ingredients of the pharmaceutical composition. For easy reference and convenience of practitioners of the present invention, the following information is incorporated in the present disclosure from a previous U.S. patent publication (US 2003/0229071 A1), the disclosure of which is incorporated herein by reference in its entirety:

"Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for oral administration can consist of (a) liquid solutions, such as an effective amount of the alkaloid dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

In a preferred embodiment, the compositions of the present invention are used in the treatment of coughs. In a preferred embodiment the invention provides a long-lasting cough composition. The dosages of the above compositions can vary depending on many factors such as the pharmacodynamic characteristics of the particular substance, and its mode and route of administration; age, health, and weight of the individual recipient; nature and extent of symptoms, kind of concurrent treatment, frequency of treatment, and the effect desired.

The compositions of the present invention preferably contain suitable pharmaceutical carriers or diluents. Suitable pharmaceutical carriers and methods of preparing pharmaceutical dosage forms are described in Remington's Pharmaceutical Sciences, Mack Publishing Company, a standard reference text in this field. Suitable pharmaceutical diluents, excipients, or carriers suitable selected with respect to the intended form of administration, that is, oral tablets, capsules, elixirs, syrups and the like, consistent with conventional pharmaceutical practices. The compositions are preferably for oral delivery, more preferably in the form of a capsule or syrup, such as a cough syrup.

For oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like. Cough formulations generally include (in addition to the active ingredients) sorbitol, saccharose, citric acid, flavoring and water.

For oral administration in the form of a tablet or capsule, the active substances can be combined with an oral, non-toxic, pharmaceutically acceptable, inert carrier such as lactose, starch, sucrose, glucose, methyl, cellulose, magnesium stearate, dicalcium phosphate, calcium sulfate, mannitol, sorbitol and the like. Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase subject acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propylparaben, and chlorobutanol.

The compounds of the invention may also be administered in the form of liposome delivery systems, such as small unilamellar vesicles, large unilamellar vesicles, and multilamelar vesicles. Liposomes can be formed from a variety of phospholipids, such as cholesterol, stearylamine, or phosphatidylcholines. The compounds of the invention may also be coupled with soluble polymers which are targetable drug carriers. Examples of such polymers include polyvinylpyrrolidone, pyran copolymer, polyhydroxypropyl-methacrylamide-phenol, polyhydroxyethylaspartamidepheno-I, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

More than one compounds of the invention may be used in a composition. The compounds can be administered concurrently, separately or sequentially.

The dose administered to a subject, in the context of the present invention should be sufficient to effect a beneficial therapeutic response in the subject over time. The dose will be determined by the condition of the subject. The size of the dose also will be determined by the existence, nature, and extent of any adverse side effects that accompany the administration to a particular subject. In determining the effective amount of alkaloid to be administered to achieve antitussive effect, standard dosing regimens may be used as known in the art. Karlsson et al., Pulmonary Pharmacology and Therapeutics (1999) 12:215-238."

While there have been described and pointed out fundamental novel features of the invention as applied to a preferred embodiment thereof, it will be understood that various omissions and substitutions and changes, in the form and details of the processes and methods illustrated, may be made by those skilled in the art without departing from the spirit of the invention. For example, it is expressly intended that all combinations of those elements of method steps which perform substantially the same function in substantially the same way to achieve the same results are within the scope of the invention.

The invention is not limited by the embodiments described above which are presented as examples only but can be modified in various ways within the scope of protection defined by the appended patent claims.

What is claimed is:

1. A method of relieving cough in a mammalian subject by administering to said subject a composition, comprising:
   an isolated compound with structure I or II:

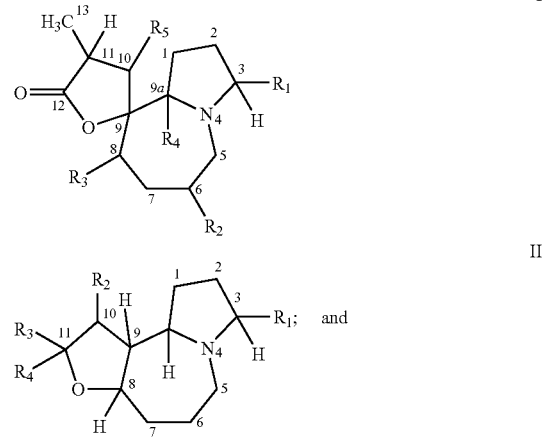

a pharmaceutically acceptable carrier,
where in said base structure I:
   $R_1$ is selected from the group consisting of hydrogen, carbonyl, hydroxyl, methoxy and α-methyl-γ-butyrolactone;
   $R_2$ is selected from the group consisting of hydrogen, hydroxyl, methoxy and oxygen bridge to $R_4$;
   $R_3$ is selected from the group consisting of hydrogen, hydroxyl and methoxy;
   $R_4$ is hydrogen or oxygen bridge to $R_2$; and
   $R_5$ is hydrogen, hydroxyl or methoxy; and
in said base structure II:
   $R_1$ is selected from the group consisting of hydrogen, carbonyl, hydroxyl, methoxy and α-methyl-γ-butyrolactone;
   $R_2$ is selected from the group consisting of hydrogen, methyl, ethyl and cyano; and
   $R_3$ and $R_4$ are each independently selected from the group consisting of H (hydrogen), =O (carbonyl), and —O—C(=O)—C(CH$_3$)=C—, which form monosubstituted spirolactone ring fused at C-11 (3-methyl-5H-furan-2-one), or —O—C(=O)—C(CH$_3$)=C(OCH$_3$)—, which form disubstituted lactone ring (4-methoxy-3-methyl-5H-furan-2-one) attached to C-11 by a double bond.

2. The method of claim 1, wherein said isolated compound is structure I, and is selected from the group consisting of Croomine, 6-Hydroxycroomine, Stemospironine, and 10-Hydroxycroomine.

3. The method of claim 1, wherein said isolated compound is structure II, and is selected from the group consisting of stemoninine and tuberostemoamide.

4. The method of claim 1, wherein said mammalian subject is a human subject.

5. The method of claim 2, wherein said mammalian subject is a human subject.

6. The method of claim 3, wherein said mammalian subject is a human subject.

7. The method of claim 1, wherein said composition is in a form selected from the group consisting of a tablet, a capsule, an injection, an elixir, and a syrup.

8. The method of claim 1, wherein said administering comprises oral delivery.

9. The method of claim 8, wherein said composition is in a form of a tablet.

10. The method of claim 8, wherein said composition is in a form of a syrup.

11. The method of claim 1, wherein said composition further comprises a liposome delivery system.

* * * * *